United States Patent
Caulkett et al.

(10) Patent No.: US 6,753,331 B1
(45) Date of Patent: Jun. 22, 2004

(54) HETEROCYCLIC DERIVATIVES WHICH INHIBIT FACTOR XA

(75) Inventors: Peter WR Caulkett, Macclesfield (GB); Roger James, Macclesfield (GB); Stuart E Pearson, Macclesfield (GB); Anthony M Slater, Macclesfield (GB); Rolf P Walker, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/674,559

(22) PCT Filed: Apr. 27, 1999

(86) PCT No.: PCT/GB99/01308

§ 371 (c)(1),
(2), (4) Date: Jan. 4, 2001

(87) PCT Pub. No.: WO99/57113

PCT Pub. Date: Nov. 11, 1999

(30) Foreign Application Priority Data

May 2, 1998 (GB) ............................................... 9809351
Feb. 16, 1999 (GB) ............................................... 9903337

(51) Int. Cl.$^7$ ...................... A61K 31/496; C07D 401/10
(52) U.S. Cl. ........................... 514/253.04; 514/253.11; 514/254.06; 514/254.09; 514/254.11; 514/299; 514/300; 514/302; 514/318; 514/320; 514/322; 514/323; 544/362; 544/364; 544/370; 544/373; 544/376; 546/113; 546/116; 546/183; 546/194; 546/196; 546/199; 546/201
(58) Field of Search ....................... 544/362, 364, 544/370, 373, 376; 546/113, 116, 183, 194, 196, 199, 201; 514/253.04, 253.11, 254.06, 254.09, 254.11, 299, 300, 302, 318, 320, 322, 323

(56) References Cited

U.S. PATENT DOCUMENTS 6,300,330 B1 * 10/2001 Stocker et al. ......... 514/252.02

FOREIGN PATENT DOCUMENTS

| WO | WO 96/10022 | 4/1996 |
| WO | WO 97/23212 | 7/1997 |
| WO | WO 97/28129 | 8/1997 |
| WO | WO 97/29104 | 8/1997 |
| WO | WO 98/21188 | 5/1998 |
| WO | WO 98/54164 | 12/1998 |
| WO | WO 99/06371 | 2/1999 |
| WO | WO 99/16751 | 4/1999 |

* cited by examiner

*Primary Examiner*—Richard L. Raymond
(74) *Attorney, Agent, or Firm*—Morgan, Lewis & Bockius, LLP

(57) ABSTRACT

The invention relates to heterocyclic derivatives of formula (I), or pharmaceutically-acceptable salts thereof, which possess antithrombotic and anticoagulant properties and are accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect.

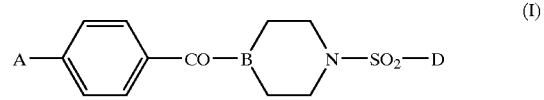

11 Claims, No Drawings

HETEROCYCLIC DERIVATIVES WHICH INHIBIT FACTOR XA

This application is the section 371 national phase of international application PCT/GB99/01308 filed Apr. 27, 1999 which designated the U.S. and that application was published under PCT Article 21(2) in English.

The invention relates to heterocyclic derivatives, or pharmaceutically-acceptable salts thereof, which possess antithrombotic and anticoagulant properties and are accordingly useful in methods of treatment of humans or animals. The invention also relates to processes for the preparation of the heterocyclic derivatives, to pharmaceutical compositions containing them and to their use in the manufacture of medicaments for use in the production of an antithrombotic or anticoagulant effect.

The antithrombotic and anticoagulant effect produced by the compounds of the invention is believed to be attributable to their strong inhibitory effect against the activated coagulation protease known as Factor Xa. Factor Xa is one of a cascade of proteases involved in the complex process of blood coagulation. The protease known as thrombin is the final protease in the cascade and Factor Xa is the preceding protease which cleaves prothrombin to generate thrombin.

Certain compounds are known to possess Factor Xa inhibitory properties and the field has been reviewed by R. B. Wallis, *Current Opinion in Therapeutic Patents*, 1993, 1173–1179. Thus it is known that two proteins, one known as antistatin and the other known as tick anticoagulant protein (TAP), are specific Factor Xa inhibitors which possess antithrombotic properties in various animal models of thrombotic disease.

It is also known that certain non-peptide compounds possess Factor Xa inhibitory properties. Of the low molecular weight inhibitors mentioned in the review by R. B. Wallis, all possessed a strongly basic group such as an amidinophenyl or amidinonaphthyl group.

We have now found that certain heterocyclic derivatives possess Factor Xa inhibitory activity. Many of the compounds of the present invention also possess the advantage of being selective Factor Xa inhibitors, that is the enzyme Factor Xa is inhibited strongly at concentrations of test compound which do not inhibit or which inhibit to a lesser extent the enzyme thrombin which is also a member of the blood coagulation enzymatic cascade.

The compounds of the present invention possess activity in the treatment or prevention of a variety of medical disorders where anticoagulant therapy is indicated, for example in the treatment or prevention of thrombotic conditions such as coronary artery and cerebro-vascular disease. Further examples of such medical disorders include various cardiovascular and cerebrovascular conditions such as myocardial infarction, the formation of atherosclerotic plaques, venous or arterial thrombosis, coagulation syndromes, vascular injury including reocclusion and restenosis following angioplasty and coronary artery bypass surgery, thrombus formation after the application of blood vessel operative techniques or after general surgery such as hip replacement surgery, the introduction of artificial heart valves or on the recirculation of blood, cerebral infarction, cerebral thrombosis, stroke, cerebral embolism, pulmonary embolism, ischaemia and angina (including unstable angina).

The compounds of the invention are also useful as inhibitors of blood coagulation in an ex-vivo situation such as, for example, the storage of whole blood or other biological samples suspected to contain Factor Xa and in which coagulation is detrimental.

The compound 1-(5-chlorobenzofuran-2-ylsulphonyl)-4-[4-(4-pyridyl)benzoyl]piperazine is disclosed as a Factor Xa inhibitor in PCT Application No.97/03033, which published after the two priority dates claimed in this application.

Accordingly in one aspect the present invention provides compounds of formula (I)

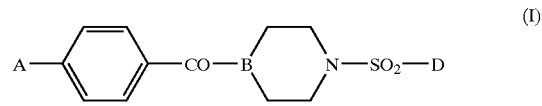

wherein:

A is a 5- or 6-membered monocyclic aromatic ring containing 1, 2 or 3 ring heteroatoms selected from nitrogen, oxygen and sulphur atoms and is unsubstituted or is substituted by one, two or three atoms or groups selected from halo (for example fluoro, chloro or bromo), oxo, carboxy, trifluoromethyl, cyano, amino, hydroxy, nitro, $C_{1-4}$alkyl (for example methyl or ethyl), $C_{1-4}$alkoxy (for example methoxy or ethoxy), $C_{1-4}$alkoxycarbonyl, $C_{1-4}$alkylamino (for example methylamino or ethylamino), di-$C_{1-4}$alkylamino (for example dimethylamino or diethylamino) or amino$C_{1-4}$alkyl (for example aminomethyl or aminoethyl);

the 1,4-phenylene ring of a compound of formula (I) is either unsubstituted or is substituted by one or two substituents selected from halo, trifluoromethyl, trifluoromethoxy, cyano, nitro, $C_{1-4}$alkyl, $C_{2-4}$alkenyl and $C_{2-4}$alkynyl, from the substituent —$(CHO_2)_n Y^1$ wherein n is 0–4 and $Y^1$ is selected from hydroxy, amino, carboxy, $C_{1-4}$alkoxy, $C_{2-4}$alkenyloxy, $C_{2-4}$alkynyloxy, $C_{1-4}$alkylamino, di-$C_{1-4}$alkylamino, pyrrolidin-1-yl, piperidino, morpholino, thiomorpholino, 1-oxothiomorpholino, 1,1-dioxothiomorpholino, piperazin-1-yl, 4-$C_{1-4}$alkylpiperazin-1-yl, $C_{1-4}$alkylthio, $C_{1-4}$alkylsulphinyl, $C_{1-4}$alkylsulphonyl, $C_{2-4}$alkanoylamino, benzamido, $C_{1-4}$alkylsulphonamido and phenylsulphonamido, from the substituent —$(CH_2)_n Y^2$ wherein n is 0–4 and $Y^2$ is selected from carboxy, carbamoyl, $C_{1-4}$alkoxycarbonyl, N—$C_{1-4}$alkylcarbamoyl, N,N-di-$C_{1-4}$alkylcarbamoyl, pyrrolidin-1-ylcarbonyl, piperidinocarbonyl, morpholinocarbonyl, thiomorpholinocarbonyl, 1-oxothiomorpholinocarbonyl, 1,1-dioxothiomorpholinocarbonyl, piperazin-1-ylcarbonyl, 4-$C_{1-4}$alkylpiperazin-1-ylcarbonyl, $C_{1-4}$alkylsulphonamidocarbonyl, phenylsulphonamidocarbonyl and benzylsulphonamidocarbonyl, from a substituent of the formula —$X^3$—$L^2$—$Y^2$ wherein $X^3$ is a group of the formula CON($R^5$), CON($L^2$—$Y^2$), C($R^5$)$_2$O, O, N($R^5$) or N($L^2$—$Y^2$), $L^2$ is $C_{1-4}$alkylene, $Y^2$ has any of the meanings defined immediately hereinbefore and each $R^5$ is independently hydrogen or $C_{1-4}$alkyl, and from a substituent of the formula —$X^3$—$L^3$—$Y^1$ wherein $X^3$ is a group of the formula CON($R^5$), CON($L^3$—$Y^1$), C($R^5$)$_2$O, O, N($R^5$) or N($L^3$—$Y^1$), $L^3$ is $C_{2-4}$alkylene, $Y^1$ has any of the meanings defined immediately hereinbefore and each $R^5$ is independently hydrogen or $C_{1-4}$alkyl, and wherein any heterocyclic group in a substituent of the 1,4-phenylene ring of compounds of formula (I) optionally bears 1 or 2 substituents selected from carboxy, carbamoyl, $C_{1-4}$alkyl, $C_{1-4}$alkoxycarbonyl, N—$C_{1-4}$alkylcarbamoyl and N,N-di-$C_{1-4}$alkylcarbamoyl, and wherein any phenyl group in a substituent of the 1,4-phenylene ring of compounds of formula 1 optionally bears 1 or 2 substituents selected from halo, trifluoromethyl, cyano, $C_{1-4}$alkyl, $C_{2-4}$alkenyl, $C_{2-4}$alkynyl, $C_{1-4}$alkoxy, $C_{2-4}$alkenyloxy and $C_{2-4}$alkynyloxy;

B is CH or N;

the heterocyclic ring containing B is either unsubstituted or is substituted by one or two substituents selected from hydroxy, oxo, carboxy and $C_{1-4}$alkoxycarbonyl; or one of the following:

—(CH$_2$)$_n$—R, —(CH$_2$)$_2$, —NRR$^1$, —CO—R, —CO—NRR$^1$, —CH$_2$)$_n$—CO—R and —(CH$_2$)$_n$—CO—NRR$^1$;

wherein n is 0, 1 or 2, preferably n is 1 or 2;

R and R$^1$ are independently selected from hydrogen, $C_{1-4}$alkyl, $C_{2-4}$alkenyl, $C_{2-4}$alkynyl, hydroxy$C_{1-4}$alkyl, carboxy$C_{1-4}$alkyl and $C_{1-4}$alkoxycarbonyl$C_{1-4}$alkyl or where possible R and R$^1$ may together form a 5- or 6-membered optionally substituted saturated or partially unsaturated (preferably unsaturated) heterocyclic ring which may include in addition to the nitrogen to which R and R$^1$ are attached 1 or 2 additional heteroatoms selected from nitrogen, oxygen and sulphur;

D is 2-indolyl, 2-benzimidazolyl, 2-benzo[b]furanyl, 2-pyrrolo[2,3-b]pyridyl, 2-furo[2,3-b]pyridyl or 6-7H-cyclopenta[b]pyridyl and is unsubstituted or is substituted by one, two or three substituents selected from halo, trifluromethyl, trifluoromethoxy, cyano, hydroxy, oxo, amino, nitro, trifluoromethylsulphonyl, carboxy, carbamoyl, $C_{1-4}$alkyl, $C_{2-4}$alkenyl, $C_{2-4}$alkynyl, $C_{1-4}$alkoxy, $C_{2-4}$alkenyloxy, $C_{2-4}$alkynyloxy, $C_{1-4}$alkylthio, $C_{1-4}$alkylsulphinyl, $C_{1-4}$alkylsulphonyl, $C_{1-4}$alkylamino, di-$C_{1-4}$alkylamino, $C_{1-4}$alkoxycarbonyl, N—$C_{1-4}$alkylcarbamoyl, N,N-di-$C_{1-4}$alkylcarbamoyl, $C_{2-4}$alkanoyl, $C_{2-4}$alkanoylamino, hydroxy$C_{1-4}$alkyl, $C_{1-4}$alkoxy$C_{1-4}$alkyl, carboxy$C_{1-4}$alkyl, $C_{1-4}$alkoxycarbonyl$C_{1-4}$alkyl, carbamoyl$C_{1-4}$alkyl, N—$C_{1-4}$alkylcarbamoyl$C_{1-4}$alkyl, N,N-di-$C_{1-4}$alkylcarbamoyl$C_{1-4}$alkyl, phenyl, heteroaryl, phenoxy, phenylthio, phenylsulphinyl, phenylsulphonyl, benzyl, benzoyl, heteroaryloxy, heteroarylthio, heteroarylsulphinyl and heteroarylsulphonyl, and wherein said heteroaryl substituent or the heteroaryl group in a heteroaryl-containing substituent is a 5- or 6-membered monocyclic heteroaryl ring containing up to 3 heteroatoms selected from nitrogen, oxygen and sulphur, and wherein said phenyl, heteroaryl, phenoxy, phenylthio, phenylsulphinyl, phenylsulphonyl, heteroaryloxy, heteroarylthio, heteroarylsulphinyl, heteroarylsulphonyl, benzyl or benzoyl substituent optionally bears 1, 2 or 3 substituents selected from halo, trifluoromethyl, cyano, hydroxy, amino, nitro, carboxy, carbamoyl, $C_{1-4}$alkyl, $C_{1-4}$alkoxy, $C_{1-4}$alkylamino, di-$C_{1-4}$alkylamino, $C_{1-4}$alkoxycarbonyl, N—$C_{1-4}$alkylcarbamoyl, N,N-di-$C_{1-4}$alkylcarbamoyl and $C_{2-4}$alkanoylamino;

and excluding the compound 1-(5-chlorobenzofuran-2-ylsulphonyl)-4-[4-(4-pyridyl)benzoyl]piperazine;

and pharmaceutically acceptable salts thereof.

For the avoidance of doubt substituents D are drawn below:

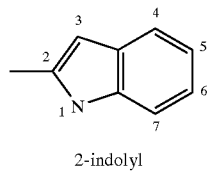

2-indolyl

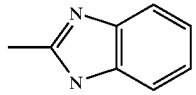

2-benzimidazolyl

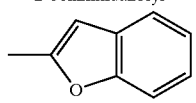

2-benzo[b]furanyl

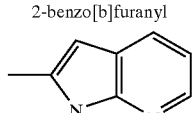

2-pyrrolo[2,3-b]pyridyl

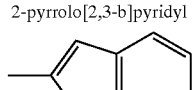

2-furo[2,3-b]pyridyl

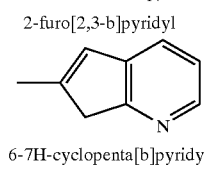

6-7H-cyclopenta[b]pyridyl

In this specification the term "alkyl" includes both straight and branched chain alkyl groups but references to individual alkyl groups such as "propyl" are specific for the straight chain version only. An analogous convention applies to other generic terms.

It is to be understood that certain heterocyclic derivatives of the present invention can exist in solvated as well as unsolvated forms such as, for example, hydrated forms. It is to be understood that the invention encompasses all such solvated forms which possess Factor Xa inhibitory activity.

It is further to be understood that, insofar as certain of the compounds of the formula defined above may exist in optically active or racemic forms by virtue of one or more asymmetric carbon atoms, the invention encompasses any such optically active or racemic form which possesses Factor Xa inhibitory activity. The synthesis of optically active forms may be carried out by standard techniques of organic chemistry well known in the art, for example by synthesis from optically active starting materials or by resolution of a racemic form.

For the avoidance "oxo" as used herein defines the substituent "=O". For the avoidance of doubt susbstituents on A may also be present, where possible, on the heteroatom of the ring, such as, for example, N-oxides.

Preferably A is an optionally substituted 5- or 6-membered monocyclic aromatic ring containing 1, 2 or 3 ring nitrogen atoms. Preferably A is a pyridyl, pyrimidinyl, imidazolyl or pyridazinyl ring for example 2-pyridyl, 3-pyridyl, 4-pyridyl, 3-pyridazinyl, 4-pyridazinyl, 4-pyrimidinyl, 5-pyrimidinyl, 1-imidazolyl, 2-imidazolyl or 4-imidazolyl. Of these 4-pyrimidinyl, 4-pyridazinyl, 1-imidazolyl, 4-imidazolyl and 4-pyridyl are preferred.

Preferred substituents of A are $C_{1-4}$alkyl, oxo, amino and halo. Preferably substituents are $C_{1-4}$alkyl, amino and halo. Preferably A is unsubstituted.

Preferably the 1,4-phenylene ring of a compound of formula 1 is substituted by carboxy, $C_{1-4}$alkoxy or $C_{1-4}$alkoxycarbonyl. Preferably the 1,4-phenylene ring of a compound of formula I is unsubstituted.

In a particular aspect the heterocyclic ring formed by R and R$^1$ on a substituent on the heterocyclic ring containing B is preferably selected from 1-pyrrolidinyl, 1-imidazolinyl, 1-piperidino, 1-piperazinyl, 4-morpholino and 4-thiomorpholino. In a particular aspect the heterocyclic ring formed by R and R¹ may be unsubstituted. In an alternative aspect the ring formed by R and R¹ is substituted by 1 or 2 substituents selected from oxo, hydroxy and carboxy. Preferably the heterocyclic ring containing B is substituted by oxo, carboxy, $C_{1-4}$alkoxy or $C_{1-4}$alkoxycarbonyl. Preferably the heterocyclic ring containing B is unsubstituted.

Preferably D is substituted by halo. Preferably the halo substituent is bromo or chloro and preferably at a position equivalent to the 5-position as numbered on the indole ring.

Suitable values for optional substituents for the 1,4-phenylene ring and D of compounds of formula 1 are:

| | |
|---|---|
| for $C_{1-4}$alkyl: | methyl, ethyl and propyl; |
| for $C_{1-4}$alkoxycarbonyl: | methoxycarbonyl, ethoxycarbonyl, propoxycarbonyl and tert-butoxycarbonyl; |
| for N-$C_{1-4}$alkylcarbamoyl: | N-methylcarbamoyl, N-ethylcarbamoyl and N-propylcarbamoyl; |
| for N,N-di-$C_{1-4}$alkylcarbamoyl: | N,N-dimethylcarbamoyl, N-ethyl-N-methylcarbamoyl and N,N-diethylcarbamoyl; |
| for hydroxy$C_{1-4}$alkyl: | hydroxymethyl, 1-hydroxyethyl, 2-hydroxyethyl and 3-hydroxypropyl; |
| for $C_{1-4}$alkoxy$C_{1-4}$alkyl: | methoxymethyl, ethoxymethyl, 1-methoxymethyl, 2-methoxyethyl, 2-ethoxyethyl and 3-methoxypropyl; |
| for carboxy$C_{1-4}$alkyl: | carboxymethyl, 1-carboxyethyl, 2-carboxyethyl and 3-carboxypropyl; |
| for $C_{1-4}$alkoxycarbonyl$C_{1-4}$alkyl: | methoxycarbonylmethyl, ethoxycarbonylmethyl, tert-butoxycarbonylmethyl, 1-methoxycarbonylethyl, 1-ethoxycarbonylethyl, 2-methoxycarbonylethyl, 2-ethoxycarbonylethyl, 3-methoxycarbonylpropyl and 3-ethoxycarbonylpropyl; |
| for carbamoyl$C_{1-4}$alkyl: | carbamoylmethyl, 1-carbamoylethyl, 2-carbamoylethyl and 3-carbamoylpropyl; |
| for N-$C_{1-4}$alkylcarbamoyl$C_{1-4}$alkyl: | N-methylcarbamoylmethyl, N-ethylcarbamoylmethyl, N-propylcarbamoylmethyl, 1-(N-methylcarbamoyl)ethyl, 1-(N-ethylcarbamoyl)ethyl, 2-(N-methylcarbamoyl)ethyl, 2-(N-ethylcarbamoyl)ethyl and 3-(N-methylcarbamoyl)propyl; |
| for N,N-di-$C_{1-4}$alkylcarbamoyl-$C_{1-4}$alkyl: | N,N-dimethylcarbamoylmethyl, N-ethyl-N-methylcarbamoylmethyl, N,N-diethylcarbamoylmethyl, 1-(N,N-dimethylcarbamoyl)ethyl, 1-(N,N-diethylcarbamoyl)ethyl, 2-(N,N-dimethylcarbamoyl)ethyl, 2-(N,N-diethylcarbamoyl)ethyl and 3-(N,N-dimethylcarbamoyl)propyl; |
| for halo: | fluoro, chloro, bromo; |
| for $C_{1-4}$alkoxy: | methoxy, ethoxy; |
| for $C_{1-4}$alkylamino: | methylamino, ethylamino: |
| for di-$C_{1-4}$alkylamino: | dimethylamino, diethylamino; |
| for $C_{1-4}$alkenyl: | vinyl and allyl; |
| for $C_{2-4}$alkynyl: | ethynyl and prop-2-ynyl; |
| for $C_{2-4}$alkenyloxy: | vinyloxy and allyloxy; |
| for $C_{2-4}$alkynyloxy: | ethynyloxy and prop-2-ynyloxy; |
| for $C_{1-4}$alkylthio: | methylthio, ethylthio and propylthio; |
| for $C_{1-4}$alkylsulphinyl: | methylsulphinyl, ethylsulphinyl and propylsulphinyl; |
| for $C_{1-4}$alkylsulphonyl: | methylsulphonyl, ethylsulphonyl and propylsulphonyl; |
| for $C_{2-4}$alkanoyl; | formyl, acetyl, proprionyl or butyryl; |
| for $C_{2-4}$alkanoylamino: | acetamido, propionamido and butyramido; |

A preferred class of compounds of the present invention is that wherein:
A is pyridyl, pyrimidinyl, imidazolyl or pyridazinyl;
B is N;
D is 2-indolyl, or 2-benzo[b]furanyl optionally substituted by fluoro, chloro or bromo;
and pharmaceutically-acceptable salts thereof.

Particular compounds of the invention include the Examples described below.

A heterocyclic derivative of formula 1, or pharmaceutically-acceptable salt thereof, may be prepared by any process known to be applicable to the preparation of related compounds. Such procedures are provided as a further feature of the invention and are illustrated by the following representative processes in which, unless otherwise stated A, B, and D have any of the meanings defined hereinbefore wherein any functional group, for example amino, alkylamino, carboxy or hydroxy, is optionally protected by a protecting group which may be removed when necessary.

Necessary starting materials may be obtained by standard procedures of organic chemistry and by reference to the processes used in the Examples.

According to another aspect, the present invention provides a process for preparing a compound of formula (I) or a pharmaceutically acceptable salt thereof, which comprises:

(a) For the production of those compounds of the formula (I) wherein B is N, the reaction, conveniently in the presence of a suitable base, of an amine of formula (II)

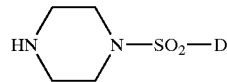

(II)

with an acid of the formula (III)

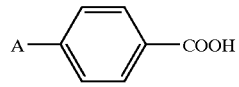

(III)

or a reactive derivative thereof.

A suitable reactive derivative of an acid of the formula (III) is, for example, an acyl halide, for example an acyl chloride formed by the reaction of the acid and an inorganic acid chloride, for example thionyl chloride; a mixed anhydride, for example an anhydride formed by the reaction of the acid with a chloroformate such as isobutyl chloroformate or with an activated amide such as 1,1'-carbonyldiimidazole; an active ester, for example an ester formed by the reaction of the acid and a phenol such as pentafluorophenol, an ester such as pentafluorophenyl trifluoroacetate or an alcohol such as N-hydroxybenzotriazole or N-hydroxysuccinimide; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethyl-carbodiimide.

The reaction is conveniently carried out in the presence of a suitable base such as, for example, an alkali or alkaline earth metal carbonate, also preferably carried out in a suitable inert solvent or diluent, for example methylene chloride, and at a temperature in the range, for example, −78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric, phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. An arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an organic acid such as trifluoroacetic acid, or for example a benzyl group which may be removed, for example, by hydrogenation over a catalyst such as palladium-on-carbon.

(b) The reaction of a compound of the formula (IV):

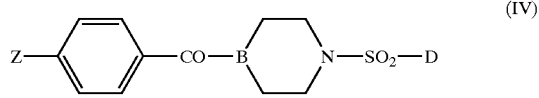

(IV)

wherein Z is a displaceable group such as halo, with an activated derivative of ring A. Suitable activated derivatives include metalised derivatives, such as with zinc or tin, and borane derivatives. The activated derivative of ring A is reacted with a compound of the formula (IV) to effect cross coupling where Z is triflate or a halo group, such as iodo, bromo or chloro. Suitably the reaction is catalysed by use of a transition state metal catalyst, such as palladium, for example tetrakis (triphenylphosphine) palladium (0).

Alternatively it is possible that ring A contains the displaceable group Z and the phenyl ring is activated, and the reaction performed as described above.

Compounds of the formula (IV) not suitable for this method are those which contain a halo substituent on any of the rings.

(c) By forming A ring on compounds of formula (IV), wherein Z is a functional group capable of cyclisation. Suitable reagents and conditions are described in Bredereck H. Chem.Ber.; 96, 1505, (1963); Fuchigami, T., Bull. Chem. Soc. Jpn., 49, p3607, (1976); Huffman, K. R., J. Org. Chem., 28, p1812, (1963); Palusso, G., Gazz. Chim. Ital., 90, p1290, (1960) and Ainsworth C., J.Het.Chem., 3, p470, (1966). Such reactions are particularly suited to the formation of 5-membered A rings. Processes suitable for synthesis of starting materials in such cyclisation reactions are described, for example, in Zhang M. Q. et al; J.Heterocyclic. Chem.; 28, 673, (1991) and Kosugi, M. et al., Bull. Chem. Soc. Jpn., 60, 767–768 (1987).

(d) The reaction of a compound of the formula (V):

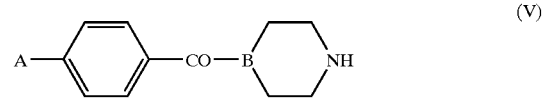

(V)

with a compound of the formula (VI):

z-SO$_2$-D (VI)

wherein Z is a displaceable group for example chloro, under conditions similar to those of process (a) above.

When a pharmaceutically-acceptable salt of a compound of the formula (I) is required, it may be obtained, for example, by reaction of said compound with a suitable acid or base using a conventional procedure.

When an optically active form of a compound of the formula (I) is required, it may be obtained, for example, by carrying out one of the aforesaid procedures using an optically active starting material or by resolution of a racemic form of said compound using a conventional procedure, for example by the formation of diastereomeric salts, use of chromatographic techniques, conversion using chirally specific enzymatic processes, or by additon of temporary extra chiral group to aid separation.

As stated previously, the compounds of the formula (I) are inhibitors of the enzyme Factor Xa. The effects of this inhibition may be demonstrated using one or more of the standard procedures set out hereinafter:

a) Measurement of Factor Xa Inhibition

An in vitro assay system based on the method of Kettner et al., *J. Biol. Chem*, 1990, 265, 18289–18297, whereby various concentrations of a test compound are dissolved in a pH7.5 buffer containing 0.5% of a polyethylene glycol (PEG 6000) and incubated at 37° C. with human Factor Xa (0.001 Units/ml, 0.3 ml) for 15 minutes. The chromogenic substrate S-2765 (KabiVitrum AB, 20 $\mu$M) is added and the mixture is incubated at 37° C. for 20 minutes whilst the absorbance at 405 nm is measured. The maximum reaction velocity (Vmax) is determined and compared with that of a control sample containing no test compound. Inhibitor potency is expressed as an IC$_{50}$ value.

b) Measurement of Thrombin Inhibition

The procedure of method a) is repeated except that human thrombin (0.005 Units/ml) and the chromogenic substrate S-2238 (KabiVitrum AB, 7 $\mu$M) are employed.

c) Measurement of Anticoagulant Activity

An in vitro assay whereby human, rat or rabbit venous blood is collected and added directly to a sodium citrate solution (3.2 g/100 ml, 9 parts blood to 1 part citrate solution). Blood plasma is prepared by centrifugation (1000 g, 15 minutes) and stored at 2–4° C. Conventional prothrombin time (PT) tests are carried out in the presence of various concentrations of a test compound and the concentration of test compound required to double the clotting time, hereinafter referred to as CT2, is determined. In the PT test, the test compound and blood plasma are incubated at 37° C. for 10 minutes. Tissue thromboplastin with calcium (Sigma Limited, Poole, England) is added and fibrin formation and the time required for a clot to form are determined.

d) Rat Disseminated Intravascular Coagulation in vivo Activity Test:

Fasted male Alderley Park rats (300–450 g) are pre-dosed by oral gavage (5 mls/kg) with compound or vehicle (5% DMSO/PEG200) at various times before being anaesthetised with Intraval® (120 mg/kg i.p.). The left jugular vein and the right carotid artery are exposed and cannulated. A 1 mL blood sample is taken from the carotid canular into 3.2% trisodium citrate. 0.5 mL of the whole blood is then treated with EDTA and used for platelet count determination whilst the remainder is centrifuged (5 mins, 20000 g) and the resultant plasma frozen for subsequent drug level, fibrinogen or thrombin antithrombin (TAT) complex determinations. Recombinant human tissue factor (Dade Innovin Cat.B4212-50), reconstituted to the manufacturers specification, is infused (2 mL/g/hr) into the venous canular for 60 minutes. Immediately after the infusion is stopped a 2 mL blood sample is taken and platelet count, drug level, plasma fibrinogen concentration and TAT complex are determined as before. Platelet counting is performed using at Coulter T540 blood analyser. Plasma fibrinogen and TAT levels are determining using a clotting assay (Sigma Cat.880-B) and TAT ELISA (Behring) respectively. The plasma concentration of the compound is bioassayed using human Factor Xa and a chromogenic substrate S2765 (Kabi), extrapolated from a standard curve (Fragmin) and expressed in Anti-Factor Xa units. The data is analysed as follows; tissue factor-induced reductions in platelet count are normalised with respect to pre-dose platelet count and drug activity expressed as a percent inhibition of tissue factor-induced thrombocytopenia when compared to vehicle treated animals. Compounds are active if there is statistically significant ($p < 0.05$) inhibition of TF-induced thrombocytopenia.

e) An ex vivo Assay of Anticoagulant Activity

The test compound is administered intravenously or orally to a group of Alderley Park Wistar rats. At various times thereafter animals are anaesthetised, blood is collected and PT coagulation assays analogous to those described hereinbefore are conducted.

f) An in vivo Measurement of Antithrombotic Activity

Thrombus formation is induced using an analogous method to that described by Vogel et al., *Thromb. Research*, 1989, 54, 399–410. A group of Alderley Park Wistar rats is anaesthetised and surgery is performed to expose the vena cava. Collateral veins are ligated and two loose sutures are located, 0.7 cm apart, round the inferior vena cava. Test compound is administered intravenously or orally. At an appropriate time thereafter tissue thromboplastin (30 μl/kg) is administered via the jugular vein and, after 10 seconds, the two sutures are tightened to induce stasis within the ligated portion of vena cava. After 10 minutes the ligated tissue is excised and the thrombus therein is isolated, blotted and weighed.

Example 1 showed an $IC_{50}$ in test a) of 0.005CM and in test b) a $C_2$ (PT) against human thrombin of 15 μM.

A feature of the invention is a compound of formula (I), or a pharmaceutically acceptable salt thereof, for use in medical therapy.

According to a further feature of the invention there is provided a pharmaceutical composition which comprises a heterocyclic derivative of formula (I), or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder such as a dry powder, a microcrystalline form or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a heterocyclic derivative of the formula (I), or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a heterocyclic derivative of formula (I), or a pharmaceutically-acceptable salt thereof, for use in a method of treatment of the human or animal body by therapy.

The invention also includes the use of such an active ingredient in the production of a medicament for use in:
  (i) producing a Factor Xa inhibitory effect;
  (ii) producing an anticoagulant effect;
  (iii) producing an antithrombotic effect;
  (iv) treating a Factor Xa mediated disease or medical condition;
  (v) treating a thrombosis mediated disease or medical condition;
  (vi) treating coagulation disorders; and/or
  (vii) treating thrombosis or embolism involving Factor Xa mediated coagulation.

The invention also includes a method of producing an effect as defined hereinbefore or treating a disease or disorder as defined hereinbefore which comprises administering to a warm-blooded animal requiring such treatment an effective amount of an active ingredient as defined hereinbefore.

The size of the dose for therapeutic or prophylactic purposes of a compound of the formula (I) will naturally vary according to the nature and severity of the medical condition, the age and sex of the animal or patient being treated and the route of administration, according to well known principles of medicine. As mentioned above, compounds of the formula (I) are useful in the treatment or prevention of a variety of medical disorders where anticoagulant therapy is indicated. In using a compound of the formula (I) for such a purpose, it will generally be administered so that a daily oral dose in the range, for example, 0.5 to 100 mg/kg body weight/day is received, given if required in divided doses. In general lower doses will be administered when a parenteral route is employed, for example a dose for intravenous administration in the range, for example, 0.01 to 10 mg/kg body weight/day will generally be used. For preferred and especially preferred compounds of the invention, in general, lower doses will be employed, for example a daily dose in the range, for example, 0.1 to 10 mg/kg body weight/day. In general a preferred dose range for either oral or parenteral administration would be 0.01 to 10 mg/kg body weight/day.

Although the compounds of formula (I) are primarily of value as therapeutic or prophylactic agents for use in warm-blooded animals including man, they are also useful whenever it is required to produce an anticoagulant effect, for example during the ex-vivo storage of whole blood or in the development of biological tests for compounds having anticoagulant properties.

The compounds of the invention may be administered as a sole therapy or they may be administered in conjunction with other pharmacologically active agents such as a thrombolytic agent, for example tissue plasminogen activator or derivatives thereof or streptokinase. The compounds of the invention may also be administered with, for example, a known platelet aggregation inhibitor (for example aspirin, a thromboxane antagonist or a thromboxane synthase inhibitor), a known hypolipidaemic agent or a known antihypertensive agent.

The invention will now be illustrated in the following Examples in which, unless otherwise stated:

(i) yields are given for illustration only and are not necessarily the maximum attainable;

(ii) the end-products have satisfactory microanalyses and their structures were confirmed by nuclear magnetic resonance (NMR) and mass spectral techniques (MS). Chemical shift values were measured on the delta scale; the following abbreviations have been used: s, singlet; d, doublet; t, triplet; q, quartet; m, multiplet;

(iii) intermediates were not generally fully characterised and purity was assessed by thin layer chromatographic, infra-red (IR) or NMR analysis; and (iv) melting points were determined using a Mettler SP62 automatic melting point apparatus or an oil-bath apparatus; melting points for the end-products of the formula 1 were generally determined after crystallisation from a conventional organic solvent such as ethanol, methanol, acetone, ether or hexane, alone or in admixture.

EXAMPLE 1

1-(5-Chlorobenzo[b]furan-2-ylsulphonyl)-4-[4-(4-pyridyl)benzoyl]piperazine

A stirred suspension of 4-(4-pyridyl)benzoic acid (133 mg, 0.67 mmol) in dimethylformamide (5 ml) was treated sequentially with 1-hydroxybenzotriazole hydrate (HOBT, 108 mg, 0.8 mmol), 1-(3-dimethylaminopropyl)-3-ethylcarbodiimide hydrochloride (EDAC, 153 mg, 0.8 mmol) and 1-(5-chlorobenzo[b]furan-2-ylsulphonyl) piperazine (201 mg, 0.67 mmol). After stirring overnight the solvent was removed in vacuo and the residue chromatographed (Merck Art 9385 silica, eluting with dichloromethane containing 2% v/v of methanol) to yield 1-(5-chlorobenzo[b]furan-2-ylsulphonyl)-4-[4-(4-pyridyl) benzoyl]piperazine as a colourless solid (40 mg), $^1$H NMR (CDCl$_3$) 3.2–3.4 ppm (broad s, 4H), 3.6–4.0 ppm (broad s, 4H), 7.35 ppm (s, 1H), 7.5 ppm (m, 6H), 7.7 ppm (m, 3H), 8.7 ppm (d, 2H), MS (M+H)$^+$ 482/484.

The requisite 1-(5-chlorobenzo[b]furan-2-ylsulphonyl) piperazine starting material was prepared as follows. A stirred solution of piperazine (1.15 g, 13.4 mmol) and triethylamine (4.7 ml, 46.5 mmol) in dichloromethane (30 ml) was cooled to ~5° C., and a solution of 5-chlorobenzo [b]furan-2-sulphonyl chloride (1.69 g, 7.8 mmol) in dichloromethane (10 ml) was added. Stirring was continued for 15 mins, and the reaction mixture then allowed to warm to ambient temperature over 2 hrs with stirring. Water was added to the reaction mixture, and the organic layer separated; this was washed with water (twice), brine (once), then dried (MgSO$_4$), filtered and evaporated to give a yellow gum. This was chromatographed (Merck Art 9385 silica, eluting with dichloromethane containing increasing amounts of methanol, up to 10% v/v) to give a yellow solid; trituration with diethyl ether gave 5-chlorobenzo[b]furan-2-ylsulphonylpiperazine as a colourless solid (1.11 g) which was used without further purification, $^1$H NMR (CDCl$_3$) 2.8–3.0 ppm (t, 4H), 3.2–3.4 ppm (t, 4H), 7.3 ppm (s, 1H), 7.45 ppm (dd, 2H), 7.7 ppm (s, 1H); MS (M+H)$^+$ 301/303.

The requisite 5-chlorobenzo[b]furan-2-sulphonyl chloride starting material was prepared as described in European Patent Application 0 355 827 (Mochida, Hydantoin derivatives).

EXAMPLE 2

1-(5-Chlorobenzo[b]furan-2-ylsulphonyl)-4-[4-(1-imidazolyl)benzoyl]piperazine

To a suspension of 4-(1-imidazolyl)benzoic acid hydrochloride (225 mg, 1 mmol.) in dimethylformamide (6 ml) was added 1-(5-chlorobenzo[b]furan-2-ylsulphonyl) piperazine (315 mg, 1.05 mmol), 1-hydroxybenzotriazole hydrate (150 mg, 1 mmol), triethylamine (0.2 ml, 1.5 mmol) and 1-(3-dimethylaminopropyl)-3-ethylcarbodi-imide hydrochloride (EDAC, 2.10 mg, 1.1 mmol), and the resultant suspension stirred overnight. The reaction mixture was poured into water, and the precipitated solid filtered off and washed with water to give (after drying) 550 mg of colourless solid.

This was purified by flash chromatography using an ISOLUTE 20 g silica column, eluting with dichlotoroethane containing methanol (2.5%), giving 330 mg of essentially pure product. This was crystallised from 2-propanol to give (220 mg, 47% yield) 1-(5-chlorobenzo[b]furan-2-ylsulphonyl)-4-[4-(1-imidazolyl)benzoyl]piperazine as colourless prisms, m.p. 175–177° C., $^1$H NMR (d$_6$DMSO) 3.3 ppm (sharp s, 4H), 3.4–3.8 ppm (broad s, 4H), 7.1 ppm (s, 1H), 7.55 ppm (d, 2H), 7.6 ppm (dd, 1H), 7.7 ppm (m, 3H), 7.8 ppm (m, 2H), 7.9 ppm (d, 1H), 8.3 ppm (s, 1H); MS (M+H)t 470/472.

The requisite 4-(1-imidazolyl)benzoic acid starting material may prepared as described in J. Med. Chem. 33 1091 (1990).

EXAMPLE 3

1-(5-Chloroindol-2-ylsulphonyl-4-[4-(4-pyridyl) benzoyl]piperazine

A stirred suspension of 4-(4-pyridyl)benzoic acid (252 mg, 1.27 mmol) in dimethylformamide (10 ml) was treated sequentially with 1-(5-chloroindol-2-ylsulphonyl)piperazine (380 mg, 1.27 mmol), 1-hydroxybenzotriazole hydrate (HOBT, 271 mg, 1.77 mmol) and 1-(3-dimethylaminopropyl)-3-ethylcarbodi-imide hydrochloride (EDAC, 291 mg, 1.52 mmol). After stirring overnight the solvent was removed in vacuo and the residue taken up in dichloromethane (50 ml). This was washed sequentially with water, saturated sodium bicarbonate solution, water and brine. Evaporation of the solvent gave a residue which was chromatographed (MPLC on Merck Art 9385 silica, gradient eluting with dichloromethane containing 0–3.5% v/v of methanol) to yield, after crystallisation from acetone, 1-(5-chloroindol-2-ylsulphonyl)-4-[4-(4-pyridyl)benzoyl]piperazine as colourless crystals (244 mg), m.p. 185–188° C., $^1$H NMR (d$_6$DMSO) 3.0–3.2 ppm (broad s, 4H), 3.4–3.8 ppm (broad s, 4H), 7.0 ppm (s, 1H), 7.3 ppm (dd, 1H), 7.5 ppm (m, 3H), 7.7 ppm (m, 2H), 7.8 ppm (m, 3H), 8.6 ppm (m, 2H), 12.4 ppm (broad s, 1H), the spectrum also contained a signal due to acetone, ca 0.5 mol. eq.; Microanalysis, found: C, 59.9; H, 4.4; N, 10.6; S, 6.1%; $C_{24}H_{21}N_4O_3ClS$. $0.5C_3H_6O$ requires: C, 60.1; H, 4.7; N, 11.0; S, 6.3%; MS (M+H)$^+$ 481/483.

The requisite 1-(5-chloroindol-2-ylsulphonyl)piperazine starting material was prepared as follows 1-(1-Benzenesulphonyl-5-chloroindol-2-ylsulphonyl)piperazine (4.15 g, 9.44 mmol) was treated with sodium hydroxide solution (32 ml of 2.5M), giving a yellow suspension. This was warmed to 80° C. with vigorous stirring and stirred for 45 mins, giving complete solution. The solution was cooled to ambient temperature and carefully treated with concentrated hydrochloric acid to pH 8; the resultant precipitate was filtered off, washed with water and dried to give 1-(5-chloroindol-2-ylsulphonyl)piperazine as a pale yellow solid, $^1$H NMR (d$_6$DMSO) 2.75 ppm (m, 4H), 2.9 ppm (m, 4H), 7.0 ppm (s, 1H), 7.3 ppm (dd, 1H), 7.5 ppm (d, 1H), 7.8 ppm (d, 1H); MS (M+H)$^+$ 300/302.

The requisite 1-(1-benzenesulphonyl-5-chloroindol-2-ylsulphonyl)piperazine starting material was prepared as follows. A solution of 1-benzenesulphonyl-5-chloroindol-2-ylsulphonyl chloride (10.0 g, 25.6 mmol) in dichloromethane (100 ml) was added dropwise to a stirred solution of piperazine (13.23 g, 6 eq.) in dichloromethane (200 ml), and the mixture stirred for a further 2 hrs. The reaction mixture was then washed with water (3×200 ml), dried (Phase-Separating paper) and evaporated to give a red oil which was purified by flash chromatography using Merck silica (Art. 9385), eluting with dichloromethane containing methanol (0–6%), to give 1-(1-benzene sulphonyl-5-chloroindol-2-ylsulphonyl)piperazine as a colourless solid, $^1$H NMR (CDCl$_3$) 2.95 ppm (m, 4H), 3.4 ppm (m, 4H), 7.4 ppm (m, 4H), 7.55 ppm (m, 2H), 8.0 ppm (d, 2H), 8.0 ppm (d, 1H); MS (M+H)$^+$ 440/442.

The requisite 1-benzene sulphonyl-5-chloroindol-2-ylsulphonyl chloride starting material may be prepared by a method analagous to that reported in J. Med. Chem. 33 749 (1990), starting from 5-chloroindole.

EXAMPLE 4

1-(5-Chloroindol-2-ylsulphonyl)-4-[4-(4-pyrimidyl)benzoyl]piperazine

By an exactly analogous method, starting from 4-(4-pyrimidyl)benzoic acid, was prepared 1-(5-chloroindol-2-ylsulphonyl)-4-[4-(4-pyrimidyl)benzoyl]piperazine as colourless crystals (230 mg) from acetone, m.p. 229–230° C., $^1$H NMR (d$_6$DMSO) 3.0–3.2 ppm (broad s, 4H), 3.4–3.8 ppm (broad s, 4H), 7.0 ppm (s, 1H), 7.3 ppm (dd, 1H), 7.5 ppm (m, 3H), 7.8 ppm (s, 1H), 8.1 ppm (d, 1H), 8.2 ppm (d, 2H), 8.9 ppm (d, 1H), 9.3 ppm (s, 1H), 12.4 ppm (broad s, 1H), the spectrum also contained a signal due to acetone, ca 0.2 mol. eq.; microanalysis, found: C, 56.7; H, 4.2; N, 14.2; S, 6.5%; $C_{23}H_{20}N_5O_3ClS$. $0.2 C_3H_6O$ requires: C, 57.1; H, 4.2; N, 14.1; S, 6.5%; MS (M+H)$^+$ 482/484.

EXAMPLE 5

1-(5-Chloroindol-2-ylsulphonyl)-4-[4-(4-pyridazinyl)benzoyl]piperazine

By an exactly analogous method, starting from 4-(4-pyridazinyl)benzoic acid, was prepared 1-(5-chloroindol-2-ylsulphonyl)-4-[4-(4-pyridazinyl)benzoyl]piperazine as colourless crystals (370 mg) from acetone, m.p. 170–172° C., $^1$H NMR (D$_6$DMSO) 3.0–3.2 ppm (broad s, 4H), 3.4–3.8 ppm (broad s, 4H), 7.0 ppm (s, 1H), 7.3 ppm (d, 1H), 7.5 ppm (m, 3H), 7.8 ppm (s, 1H), 7.95 ppm (d, 2H), 8.0 ppm (dd, 1H), 9.3 ppm (d, 1H), 9.6 ppm (s, 1H), 12.4 ppm (broad s, 1H), the spectrum also contained a signal due to acetone, ca 1.0 mol. eq.; MS (M+H)$^+$ 482–484.

EXAMPLE 6

1-(5-Chloroindol-2-ylsulphonyl)-4-[4-(1-imidazolyl)benzoyl]piperazine

By an analogous method, starting from 4-(1-imidazolyl)benzoic acid hydrochloride and 1-(5-chloroindol-2-ylsulphonyl)piperazine, was prepared 1-(5-chloroindol-2-ylsulphonyl)-4-[4-(1-imidazolyl)benzoyl]piperazine (375 mg, 60% yield) as colourless crystals from acetone; m.p. 155–165° C., $^1$H NMR (d$_6$DMSO) 3.0–3.2 ppm (broad s, 4H), 3.4–3.8 ppm (broad s, 4H), 7.0 ppm (s, 1H), 7.1 ppm (s, 1H), 7.3 ppm (dd, 1H), 7.5 ppm (m, 3H), 7.7 ppm (d, 2H), 7.8 ppm (m, 2M), 8.3 ppm (s, 1H), 12.4 ppm (broad s, 1H), the spectrum also contained a signal due to acetone, ca 0.05 mol. eq.; MS (M+H)$^+$ 470/472.

EXAMPLE 7

1-(6-Chloroindol-2-ylsulphonyl)-4-[4-(4-pyridylabenzoyl]piperazine

By an exactly analogous method, starting from 4-(4-pyridyl)benzoic acid and 1-(6-chloroindol-2-ylsulphonyl)piperazine, was prepared 1-(6-chloroindol-2-ylsulphonyl)-4-[4-(4-pyridyl)benzoyl]piperazine as colourless crystals (145 mg) from acetone, m.p. 231–234° C., $^1$H NMR (d$_6$DMSO) 3.0–3.2 ppm (broad s, 4H), 3.4–3.8 ppm (broad s, 4H), 7.1 ppm (s, 1H), 7.2 ppm (dd, 1H), 7.5 ppm (m, 3H), 7.7 ppm (m, 3H), 7.8 ppm (d, 2H), 8.6 ppm (d, 2H), 12.4 ppm (broad s, 1H), the spectrum also contained a signal due to acetone, ca 0.25 mol. eq.; MS (M+H)$^+$ 481/483.

The requisite 1-(6-chloroindol-2-ylsulphonyl)piperazine starting material was prepared as follows. 1-(1-Benzenesulphonyl-6-chloroindol-2-ylsulphonyl)piperazine (500 mg, 1.18 mmol) was treated with sodium hydroxide solution (4 ml of 10M), and the suspension refluxed for 2 hrs. The reaction mixture was cooled to ambient temperature and carefully treated with concentrated hydrochloric acid to pH 8; the resultant precipitate was filtered off, washed with water and dried to give 1-(6-chloroindol-2-ylsulphonyl)piperazine as a pale yellow solid which was used without further purification; $^1$H NMR (d$_6$DMSO) 3.1 ppm (m, 4H), 3.2 ppm (m, 4H), 7.1 ppm (s, 1H), 7.2 ppm (dd, 1H), 7.5 ppm (s, 1H), 7.7 ppm (d, 1H); the spectrum also contained signals due to benzene sulphonic acid (ca 25 mol %); MS (M+H)$^+$ 300/302.

The requisite 1-(1-benzenesulphonyl-6-chloroindol-2-ylsulphonyl)piperazine starting material was prepared as follows. A solution of 1-benzene sulphonyl-6-chloroindol-2-ylsulphonyl chloride (5.0 g, 12.8 mmol) in dichloromethane (50 ml) was added dropwise to a stirred solution of piperazine (6.62 g, 6 eq.) in dichloromethane (100 ml), and the mixture stirred for a further 4 hrs. giving a yellow solution. This was then evaporated and dried overnight under high vacuum. The residue was purified by flash chromatography using Merck silica (Art. 9385), eluting with dichloromethane containing methanol (06%), to give 1-(1-benzenesulphonyl-6-chloroindol-2-ylsulphonyl)piperazine as an off-white solid (3.68 g, 68% yield); $^1$H NMR (CDCl$_3$) 2.75 ppm (m, 4H), 3.3 ppm (m, 4H), 7.45 ppm (d, 1H), 7.6 ppm (m, 3H), 7.7 ppm (m, 1H), 7.75 ppm (d, 1H), 8.0 ppm (d, 2H), 8.15 ppm (s, 1H); MS (M+H)$^+$ 440/442.

The requisite 1-benzenesulphonyl-6-chloroindol-2-ylsulphonyl chloride starting material may be prepared by a method analagous to that reported in J. Med. Chem. 33 749 (1990), stating from 6-chloroindole.

EXAMPLE 8

1-(4-Chlorobenzimidazol-2-ylsulphonyl)-4-[4-(4-pyridyl)benzoyl]piperazine

A solution of 1-(5-chlorobenzimidazol-2-ylsulphonyl)-4-(t-butyloxycarbonyl)piperazine (860 mg, 2.15 mmol) in dichloromethane/methanol (15 ml of 1:1) was treated with an excess of hydrogen chloride gas as a saturated solution in ethyl acetate. After stirring for 4 hrs. the solvent was removed in vacuo and the residue dried under high vacuum. This was then suspended in DMF and treated sequentially with 4-(4-pyridyl)benzoic acid (428 mg, 2.15 mmol), triethylamine (0.6 ml, 4.3 mmol) and 1-(3-dimethylaminopropyl)-3-ethylcarbodiimide hydrochloride (EDAC, 495 mg, 2.68 mmol). After stirring overnight the solvent was removed in vacuo and the residue taken up in dichloromethane (50 ml). This was washed sequentially with water, saturated sodium bicarbonate solution, water and brine. Evaporation of the solvent gave a residue which was purified by chromatography (MPLC on Merck Art 9385 silica, gradient eluting with ethyl acetate containing 0–8.0% methanol) to give 1-(5-chlorobenzimidazol-2-ylsulphonyl)-4-[4-(4-pyridyl)benzoyl]piperazine as colourless crystals (370 mg) from ethanol, m.p. 242–244° C., $^1$H NMR (d$_6$DMSO) 3.0–3.4 ppm (broad s, 4H), 3.4–3.8 ppm (broad s, 4H), 7.4 ppm (d, 1H), 7.5 ppm (d, 2H), 7.6–7.8 ppm (m, 4H), 7.85 ppm 2H), 8.6 ppm (d, 2H), 14.0 ppm (broad s, 1H); MS (M+H)$^+$ 482/484.

The requisite 1-(5-chlorobenzimidazol-2-ylsulphonyl)-4-(t-butyloxycarbonyl)piperazine starting material was prepared as follows. A suspension of 5-chloro-2-thiolbenzimidazole (500 mg, 2.71 mmol) in acetic acid (2.5 ml) and water (10 ml) was cooled to 5° C. and chlorine gas bubbled in slowly, keeping the temperature below 7° C. The flow of chlorine was maintained until no more was absorbed, and then for a further 15 mins., after which time the reaction was purged with argon. The suspension was filtered off, washed quickly with water and then added in small portions to a stirred, cooled (5° C.) solution of N-Boc piperazine (1.26 g, 6.78 mmol) in dichloromethane (20 ml). After stirring for 1 hr. At ambient temperature, the reaction mixture was diluted with more dichloromethane (30 ml) and washed sequentially with citric acid solution (30 ml, 1M), sat. brine (30 ml), water (2×30 ml) and sat. brine (30 ml). The solution was dried (Phase-Sep paper) and evaporated to give 1-(5-chlorobenzimidazol-2-ylsulphonyl)4-(t-butyloxycarbonyl)piperazine as a brown foam (880 mg, 81% yield), which was used without further purification; $^1$H NMR (CDCl$_3$) 1.4 ppm (s, 9H), 3.4 ppm (m, 4H), 3.6 ppm (m, 4H), 7.4 ppm (d, 1H), 7.4–7.6 ppm (broad s, 1H), 7.7–7.9 ppm (broad s, 1H); MS (M+H)$^+$ 401/403 (w), (M+H−56)$^+$ 345/347 (s).

EXAMPLE 9

1-(5-Bromoindol-2-ylsulphonyl)-4-[4-(4-pyridyl)benzoyl]piperazine

By a method analogous to that described in Example 3 starting from 4-(4-pyridyl)benzoic acid (199 mg, 1 mmol) and 1-(5-bromoindol-2-ylsulphonyl)piperazine (344 mg, 1 mmol, 1 mol eq.), was prepared 1-(5-bromoindol-2-ylsulphonyl)-4-[4-(4-pyridyl)benzoyl]piperazine methane sulphonic acid salt, (155 mg), $^1$H NMR (d$_6$-DMSO) 2.3 (s, 3H), 3.0–3.3 (broad d, 4H), 3.4–3.8 (broad d, 4H), 7.0 (d, 1H), 7.45 (s, 2H), 7.6 (d, 2H), 7.95 (s, 1H), 8.0 (d, 2H), 8.25 (d, 2H), 8.9 (d, 2H), 12.4 (s, 1H), signals were also present due to ethanol (0.15 mol equiv.); MS (M+H)$^+$ 525/527.

EXAMPLE 10

1-(5-Chloroindol-2-ylsulphonyl)-4-[4-(6-oxo-1H-pyridazin-3-yl)benzoyl]piperazine By a method analogous to that described in Example 3 starting from 4-(6-oxo-1H-pyridazin-3-yl)benzoic acid (302 mg, 1.4 mmol) and 1-(5-chloroindol-2-ylsulphonyl) piperazine (419 mg, 1.4 mmol, 1.0 mol eq.) was prepared 1-(5-chloroindol-2-ylsulphonyl)-4-[4-(6-oxo-1H-pyridazin-3-yl)benzoyl]piperazine(234 mg) as an off white solid. $^1$H NMR (300 MHz, d$_6$-DMSO) 3.1 (s, 4H, under H$_2$O), 3.6 (bs, 4H), 6.9 (d, 1H), 7.0 (s, 1H), 7.3 (dd, 1H), 7.4 (d, 2H), 7.5 (d, 1H), 7.8 (s, 1H), 7.9 (d, 2H), 8.0 (d, 1H), 12.2 (bs, 1H), 13.1 (br, 1H), signals were also present due to dichloromethane (1 mol equ.); MS (MH)$^-$ 496/498. 4-(3-1H-pyrazin-6-onyl)-benzoic acid was prepared by the method described by: Coates, W. J.; McKillop, A., Synthesis, 1993, 334–342.

EXAMPLE 11

Method A

The reaction is performed in a manner analogous to that described in Example 2, using the appropriate starting materials.

Method B

In a typical example excess methylamine gas (or other appropriate amine) was added to a solution of 1-(5-chloroindol-2-ylsulphonyl)-4-[(6-methylsulfonylpyrimidin-4-yl)benzoyl]piperazine (or the 2-methylsulfonylpyrimidinyl isomer) in THF or similar appropriate solvent. The solution was stirred at ambient or elevated temperature until TLC analysis indicated that the starting material had been consumed. The solution was concentrated in vacuo and the residue purified by column chromatography on silica. Where appropriate, he resultant free base was dissolved in 2:1 dichloromethane/methanol (20 mL) and treated with excess methanolic hydrogen chloride. The mixture was concentrated in vacuo to give the product as a near colourless foam, which could be crystallised, typically from aqueous ethanol.

Method C

To a solution of 1-(5-chloroindol-2-ylsulphonyl)-4-[(2-tert-butyloxypyrimidin-4-yl)benzoyl]piperazine (200 mg, 0.361 mmol) in dichloromethane and methanol (10 ml of a 4:1 mixture) was added a solution of hydrogen chloride in methanol (0.40 ml of ~4.5 M, 1.8 mmol), and the reaction stirred at ambient temperature for 1 hr. The solvent was removed in vacuo and the residue crystallised from ethanol to give 1-(5-chloroindol-2-ylsulphonyl)-4-[(2-hydroxypyrimidin-4-yl)benzoyl]piperazine as a colourless solid.

From the above methods the following examples were prepared:

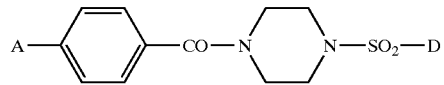

| No | A | D | Method | MS: m/z | $^1$H NMR (NMR, solvent) |
|---|---|---|---|---|---|
| 1 | 4-pyridyl | 5-fluoro-2-indolyl | A | (M + H)$^+$ 465. | $^1$H NMR (d$_6$DMSO) 3.0-3.2 ppm (broad s, 4H), 3.4-3.7 ppm (broad s, 4H), 7.0 ppm (s, 1H), 7.2 ppm (t of d, 1H), 7.5 ppm (m, 4H), 7.7 ppm (d, 2H), 7.8 ppm (d, 2H), 8.6 ppm (d, 2H), 12.3 ppm (broad s, 1H); the spectrum also contained signals due to acetone (0.33 mol eq). |
| 2 | 4-pyridyl | 5-bromo-2-indolyl | A | (M + H)$^+$ 525/527. | $^1$H NMR (d$_6$DMSO) 2.3 ppm (s, 3H), 3.3-3.5 ppm (broad s, 4H), 3.5-3.8 ppm (broad s, 4H), 70 ppm (s, 1H), 7.4 ppm (s, 2H), 7.6 ppm (d, 2H), 7.9 ppm (s, 1H), 8.0 ppm (d, 2H), 8.3 ppm (d, 2H), 8.9 ppm (d, 2H), 12.3 ppm (broad s, 1H); the spectrum also contained signals due to ethanol (0.15 mol eq). |
| 3 | 2-pyridyl | 5-chloro-2-indolyl | A | (M + H)$^+$ 481/483 | $^1$H NMR (d$_6$DMSO) 3.0-3.2 ppm (broad s, 4H), 3.4-3.8 ppm (broad s, 4H), 7.0 ppm (s, 1H), 7.3 ppm (m, 2H), 7.5 ppm (m, 3H), 7.8 ppm (s, 1H), 7.9 ppm (m, 1H), 8.0 ppm (d, 1H), 8.1 ppm (d, 2H), 8.7 ppm (d, 1H), 12.4 ppm (broad s, 1H); the spectrum also contained signals due to ethanol (1 mol eq). |
| 4 | 1-imidazolyl | 5-bromo-2-indolyl | A | (M + H)$^+$ 514/516 | $^1$H NMR (d$_6$DMSO) 2.9-3.2 ppm (broad s, 4H), 3.2-3.8 ppm (broad s, 4H), 7.0 ppm (s, 1H), 7.4 ppm (dd, 2H), 7.6 ppm (d, 2H), 7.8 ppm (s, 1H and d, 2H), 7.9 ppm (s, 1H), 8.3 ppm (s, 1H), 9.6 ppm (s, 1H), 12.4 ppm (broad s, 1H); the spectrum also contained signals due to ethanol (0.15 mol eq). |
| 5 | 2-methyl-1-imidazolyl | 5-chloro-2-indolyl | A | (MH)$^+$ 484/486 (1 × Cl) | $^1$H NMR(d$_6$DMSO) 2.54 ppm (s, 3H), 3.14 ppm (s, 4H), 3.56 ppm (s, 4H), 7.01 ppm (s, 1H), 7.29 ppm (d, 1H), 7.52 ppm (d, 1H), 7.61 ppm (m, 6H), 7.74 ppm (s, 2H). |
| 6 | 2-imidazolyl | 5-chloro-2-indolyl | A | (MH)$^+$ 470/472 (×Cl) | $^1$H NMR(d$_6$-DMSO) 2.54-3.19 ppm (broad s, 4H), 3.67 ppm (broad s, 4H), 7.01 ppm (s, 1 H), 7.31 ppm (dxd, 1H), 7.50 ppm (d, 1H), 7.60 ppm (d, 2H), 7.78 ppm (d, 2H), 7.80 ppm (s, 1H), 8.14 ppm (d, 2H), 12.41 (broad s, 1H). |
| 7 | 4-imidazolyl | 5-chloro-2-indolyl | A | (M + H)$^+$ 470/472. | $^1$H NMR (d$_6$DMSO) 3.05-3.15 ppm (broad s, 4H), 3.5-3.7 ppm (broad s, 4H), 7.0 ppm (s, 1H), 7.3 ppm (dd, 2H), 7.5 ppm (m, 3H), 7.8 ppm (m, 3H), 8.15 ppm (s, 1H), 9.0 ppm (s, 1H), 12.4 ppm (broad s, 1H). |
| 8 | 4-imidazolyl | 5-bromo-2-indolyl | A | (M + H)$^+$ 514/516. | $^1$H NMR (d$_6$DMSO) 2.3 ppm (s, 3H), 3.2-3.8 ppm (broad s, 8H), 7.0 ppm (s, 1H), 7.45 ppm (d, 2H), 7.5 ppm (d, 2H), 7.8 ppm (d, 2H), 7.9 ppm (s, 1H), 8.2 ppm (s, 1H), 9.2 ppm (s, 1H), 12.4 ppm (broad s, 1H). |
| 9 | 1-methyl-4-imidazolyl | 5-chloro-2-indolyl | A | (M + H)$^+$ 484/486. | $^1$H NMR (d$_6$DMSO) 3.0-3.2 ppm (broad s, 4H), 3.3-3.8 ppm (broad s, 4H), 3.9 ppm (s, 3H), 7.0 ppm (s, 1H), 7.3 ppm (dd, 1H), 7.5 ppm (m, 3H), 7.8 ppm (s, 1H), 7.9 ppm (d, 2H), 8.2 ppm (s, 1H), 9.15 ppm (s, 1H), 12.4 ppm (broad s, 1H); the spectrum also contained signals due to acetone (0.5 mol eq). |
| 10 | 2-methyl-4-imidazolyl | 5-chloro-2-benzofuranyl | A | (M + H)$^+$ 485/487. | $^1$H NMR (d$_6$DMSO) 2.6 ppm (s, 3H), ~3 ppm (broad s, 4H), 3.4-3.8 ppm (broad s, 4H), 7.5 ppm (d, 2H), 7.6 ppm (dd, 1H), 7.65 ppm (s, 1H), 7.8 ppm (m, 3H), 7.9 ppm (d, 1H), 8.1 ppm (s, 1H). |
| 11 | 2-methyl-4-imidazolyl | 5-chloro-2-indolyl | A | (M + H)$^+$ 484/486. | $^1$H NMR (d$_6$DMSO) 2.3 ppm (s, 3H), 3.0-3.1 ppm (broad s, 4H), 3.5-3.7 ppm (broad s, 4H), 7.0 ppm (s, 1H), ~7.3 ppm (m, 3H), 7.5 ppm (d, 2H), 7.7 ppm (br d, 2H), 7.8 ppm (d, 1H), 11.85 ppm (broad s, 1H), 12.4 ppm (broad s, 1H). |
| 12 | 2-methyl-4-imidazolyl | 5-bromo-2-indolyl | A | (M + H)$^+$ 528/530. | $^1$H NMR (d$_6$DMSO) 2.6 ppm (s, 3H), 3.0-3.2 ppm (broad s, 4H), 3.6-3.9 ppm (broad s, 4H), 7.0 ppm (s, 1H), 7.4-7.5 ppm (m, 4H), 7.85 ppm (d, 2H), 7.95 ppm (s, 1H), 8.1 ppm (s, 1H), 12.4 ppm (s, 1H), 14.3-15.0 ppm (broad s, 1H); the spectrum also contained signals due to ethanol (0.5 mol eq). |
| 13 | 2-amino-4-imidazolyl | 5-chloro-2-indolyl | A | (MH)$^+$ 485/487 (1 × Cl) | $^1$H NMR (d$_6$DMSO) 3.10 ppm (s, 4H), 3.55 ppm (broad s, 4H), 7.02 ppm (s, 1H), 7.32 ppm (dxd, 1H), 7.42 ppm (d, 2H), 7.48 ppm (m, 2H), 7.65 ppm (m, 4H), 7.80 ppm (d, 1H), 12.21 ppm (broad s, 1H), 12.43 ppm (d, 1H), 12.92 ppm (broad s, 1H). |
| 14 | 6-hydroxy-3-pyridazinyl | 5-chloro-2-indolyl | A | (MH)$^+$ 496/498 (1 × Cl) | $^1$H NMR (d$_6$DMSO) 3.10 ppm (s, 4H, under H$_2$O), 3.57 ppm (broad s, 4H), 6.95 ppm (d, 1H), 7.02 ppm (s, 1H), 7.31 ppm (dxd, 1H), 7.43 ppm (d, 2H), 7.49 ppm (d, 1H), 7.75 ppm (s, 1H), 7.85 ppm (d, 2H), 7.98 ppm (d, 1H), 12.23 ppm (s, 1H), 13.08 ppm (s, 1H). Signal also present consistent with dichloromethane (1 mol). |
| 15 | 6-hydroxy-3 pyridazinyl | 5-chloro-2-benzofuranyl | A | (MH)$^+$ 499/501 (1 × Cl) | $^1$H NMR (d$_6$DMSO) 3.21 ppm (s, 4H, under H$_2$O), 3.46 ppm (broad s, 4H), 6.92 ppm (d, 1H), 7.42 ppm (d, 2H), 7.53 ppm (d, 1H), 7.59 ppm (d, 1H), 7.76 ppm (s, 1H), 7.81 ppm (m, 3H), 7.96 ppm (d, 2H), 13.14 ppm (s, 1H) ppm |
| 16 | 6-hydroxy-3 pyridazinyl | 5-chloro-2-benzimidazolyl | A | (MH)$^+$ 499/501 (1 × Cl) | $^1$H NMR (d$_6$DMSO) 3.42 ppm (s, 4H, under H$_2$O), 3.64 ppm (s, 4H), 6.98 ppm (d, 1H), 7.39 ppm (d, 1H), 7.50 ppm (d, 2H), 7.75 ppm (m, 2H), 7.89 ppm (d, 2H), 7.96 ppm (d, 1H), 12.92 ppm (s, 1H). |

-continued

| No | A | D | Method | MS: m/z | $^1$H NMR (NMR, solvent) |
|---|---|---|---|---|---|
| 17 | 6-dimethylamino-3-pyridazinyl | 5-chloro-2-indolyl | A | (MH)$^+$ 525/527 (1 × Cl) | $^1$H NMR (d$_6$DMSO) 3.12 ppm (s, 4H), 3.25 ppm (s, 6H), 3.59 ppm (broad s, 4H, under water), 7.01 ppm (s, 1H), 7.32 ppm (dxd, 1H), 7.50 ppm (m, 3H), 7.70 ppm (d, 1H), 7.78 ppm (s, 1AH), 8.04 ppm (d, 2H), 8.28 ppm (d, 1H), 12.42 ppm (s, 1H). |
| 18 | 6-chloro-3-pyridazinyl | 5-chloro-2-indolyl | A | (MH)$^+$ 523/525 (1 × Cl) | $^1$H NMR (d$_6$DMSO) 1.43 ppm (m, 2H), 1.60 ppm (m, 2H), 2.89 ppm (m, 3H), 2.97 ppm (s, 4H), 3.52 ppm (s, 2H), 3.62 ppm (s, 2H), 4.23 ppm (d, 2H), 7.00 ppm (s, 1H), 7.30 ppm (m, 2H), 7.45 ppm (t, 2H), 7.76 ppm (d, 1H). |
| 19 | 6-amino-3-pyridazinyl | 5-chloro-2-indolyl | A | (MH)$^+$ 497/499 (1 × Cl) | $^1$H NMR (d$_6$DMSO) 3.13 ppm (s, 4H), 3.59 ppm (broad s, 4H under water), 7.03 ppm (s, 1H), 7.33 ppm (d, 1H), 7.40 ppm (d, 1H), 7.49 ppm (m, 3H), 7.79 ppm (s, 1H), 7.96 ppm (d, 2H), 8.19 ppm (broad s, 2H), 8.27 ppm (d, 1H) 12.41 ppm (s, 1H). |
| 20 | 6-methylamino-3-pyridazinyl | 5-chloro-2-indolyl | A | (MH)$^+$ 522/524 (1 × Cl) | $^1$H NMR (d$_6$DMSO) 2.38 ppm (s, 3H), 3.17 ppm (m, 4H), 3.58 ppm (m, 4H under water), 7.00 ppm (s, 1H), 7.28 ppm (dxd, 1H), 7.53 ppm (t, 4H), 7.73 ppm (s, 1H), 7.97 ppm (d, 2H), 8.21 ppm (d, 1H), 12.10 ppm (broad s, 1H). |
| 21 | 6-dimethylamino-4-pyrimidinyl | 5-chloro-2-indolyl | B | 525.2/527.1 (M + H)$^+$ | $^1$H NMR (d$_6$DMSO) 2.95-3.25 ppm (m, 5H), 3.32 ppm (s, 6H), 3.32-3.85 ppm (m, 4H under water), 7.00 ppm (s, 1H), 7.25-7.35 ppm (m, 2H), 7.45-7.55 ppm (d, 1H), 7.55-7.62 ppm (d, 2H), 7.80 ppm (s, 1H), 8.00-8.10 ppm (d, 2H), 8.80 ppm (s, 1H), 12.5 ppm (s, 1H) spectrum contains iso-propanol. |
| 22 | 6-amino-4-pyrimidinyl | 5-chloro-2-indolyl | B | (MH)$^+$ 497/499 (1 × Cl) | $^1$H NMR (d$_6$DMSO) 2.9-3.3 ppm (broad s, 4H), 3.5-4.0 ppm (broad s, 4H), 7.0 ppm (s, 1H and s, 1H), 7.3 ppm (dd, 1H), 7.5 ppm (d, 1H), 7.6 ppm (d, 2H), 7.8 ppm (s, 1H), 7.9 ppm (d, 2H), 8.7 ppm (s, 1H), 8.8 ppm (br s, 2H), 12.4 ppm (s, 1H). |
| 23 | 6-methylamino-4-pyrimidinyl | 5-chloro-2-indolyl | B | (MH)$^+$ 511/513 (1 × Cl) | $^1$H NMR (300 MHz, d$_6$-DMSO) 2.32 (s, 3H), 3.05 (broad s, 4H), 3.30-3.85 (m, 4H), 6.94-7.05 (m, 1.7H), 7.14 (s, 0.3H), 7.32 (dd, 1H), 7.50 (d, 1H), 7.62 (d, 2H), 7.75-7.91 (m, 2.3H), 7.95-8.07 (m, 0.7H), 8.70 (s, 0.3H), 8.86 (s, 0.7H), 9.37 (s, 1H), 12.38 (s, 1H) ppm. |
| 24 | 2-hydroxy-5-pyrimidinyl | 5-chloro-2-indolyl | C | (MH)$^+$ 498/500 (1 × Cl) | $^1$H NMR (d$_6$DMSO) 3.0-3.2 ppm (broad s, 4H), 3.4-3.7 ppm (broad s, 4H), 7.0 ppm (d, 1H), 7.3 ppm (dd, 1H), 7.4 ppm (d, 2H), 7.5 ppm (d, 1H), 7.65 ppm (d, 2H), 7.8 ppm (s, 1H), 8.6 ppm (br s, 2H), 12.4 ppm (s, 1H); the spectrum also contained signals due to ethanol (0.5 mol eq). |

What is claimed is:

1. A compound of formula (I)

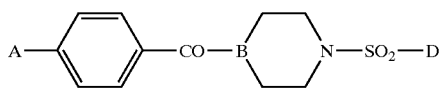

(I)

wherein:

A is a 5- or 6-membered monocyclic aromatic ring containing 1, 2 or 3 ring heteroatoms selected from nitrogen, oxygen and sulphur atoms and is unsubstituted or is substituted by one, two or three atoms or groups selected from halo, oxo, carboxy, trifluoromethyl, cyano, amino, hydroxy, nitro, C$_{1-4}$alkyl, C$_{1-4}$alkoxy, C$_{1-4}$alkoxycarbonyl, C$_{1-4}$alkylamino, di-C$_{1-4}$alkylamino or aminoC$_{1-4}$alkyl;

B is N; and

D is 2-indoly, or a pharmaceutically-acceptable salt thereof.

2. A compound of formula (I) as claimed in claim 1 wherein A is a pyridyl, pyrimidinyl, imidazolyl or pyridazinyl ring;

or a pharmaceutically-acceptable salt thereof.

3. A compound of formula (I) as claimed in claim 2 wherein A is 2-pyridyl, 3-pyridyl, 4-pyridyl 3-pyradazinyl, 4-pyridazinyl, 4-pyrimidinyl, 5-pyrimidinyl, 1-imidazolyl, 2-imidazolyl or 4-imidazolyl;

or a pharmaceutically-acceptable salt thereof.

4. A compound of formula (I) as claimed in claim 1 wherein A is substituted by C$_{1-4}$alkyl, amino and halo;

or a pharmaceutically-acceptable salt thereof.

5. A compound of formula (I) as claimed in claim 1 wherein A is unsubstituted;

or a pharmaceutically-acceptable salt thereof.

6. A compound of formula (I) as claimed in claim 1 wherein D is substituted by bromo or chloro;

or a pharmaceutically-acceptable salt thereof.

7. A compound of formula (I) as claimed in claim 1 wherein:

A is pyridyl, pyrimidinyl, imidazolyl or pyridazinyl;

B is N;

D is 2-indolyl optionally substituted by fluoro, chloro or bromo;

or a pharmaceutically-acceptable salt thereof.

8. 1-(5-Chloroindol-2-ylsulphonyl)-4-[4-(4-pyridyl) benzoyl]piperazine or a pharmaceutically-acceptable salt thereof.

9. 1-(5-Chloroindol-2-ylsulphonyl)-4-[4-(1-imidazolyl) benzoyl]piperazine or a pharmaceutically-acceptable salt thereof.

10. A pharmaceutical composition comprising a compound of formula (I), or a pharmaceutically-acceptable salt thereof, as defined in any one of claims 1–5 or 6–9, with a pharmaceutically-acceptable diluent or carrier.

11. A method of treating a Factor Xa mediated disease or condition in a warm-blooded animal comprising administering an effective amount of a compound of formula (I), as defined in any one of claims 1–5 or 6–9, or a pharmaceutically-acceptable salt thereof.

* * * * *